(12) United States Patent
McStay et al.

(10) Patent No.: US 8,927,924 B2
(45) Date of Patent: Jan. 6, 2015

(54) OPTICAL LEAK DETECTOR FOR SUBSEA EQUIPMENT

(75) Inventors: Daniel McStay, Aberdeenshire (GB); Laurie Costello, Edinburgh (GB); David Kane, Edinburgh (GB)

(73) Assignee: FMC Technologies, Inc., Houston, TX (US)

( * ) Notice: Subject to any disclaimer, the term of this patent is extended or adjusted under 35 U.S.C. 154(b) by 684 days.

(21) Appl. No.: 13/254,007

(22) PCT Filed: Mar. 6, 2009

(86) PCT No.: PCT/IB2009/000529
§ 371 (c)(1),
(2), (4) Date: Dec. 19, 2011

(87) PCT Pub. No.: WO2010/100522
PCT Pub. Date: Sep. 10, 2010

(65) Prior Publication Data
US 2012/0091364 A1  Apr. 19, 2012

(51) Int. Cl.
*G01N 21/85* (2006.01)
*G01M 3/20* (2006.01)
*G01M 3/38* (2006.01)

(52) U.S. Cl.
CPC . *G01M 3/20* (2013.01); *G01M 3/38* (2013.01); *G01N 21/8507* (2013.01)
USPC ........................................................ 250/259

(58) Field of Classification Search
USPC ........................................................ 250/259
See application file for complete search history.

(56) References Cited

U.S. PATENT DOCUMENTS

| 4,626,693 | A  | * | 12/1986 | Hirschfeld | ................. | 250/458.1 |
| 4,782,234 | A  |   | 11/1988 | Chudyk et al. | | |
| 5,444,803 | A  | * | 8/1995 | Kim et al. | ........................ | 385/28 |
| 8,264,692 | B2 | * | 9/2012 | Hall | .............................. | 356/478 |
| 2007/0107907 | A1 | * | 5/2007 | Smedstad et al. | ............. | 166/357 |
| 2009/0132183 | A1 | * | 5/2009 | Hartog et al. | ................... | 702/42 |

FOREIGN PATENT DOCUMENTS

| GB | 2 176 604 A | 12/1986 |
| GB | 2 405 467 A | 3/2005 |
| WO | WO2009/029428 | 3/2009 |

OTHER PUBLICATIONS

PCT Search Report and Written Opinion from PCT/IB09/00529 dated Nov. 12, 2009.

* cited by examiner

*Primary Examiner* — Casey Bryant
(74) *Attorney, Agent, or Firm* — Amerson Law Firm, PLLC (57) ABSTRACT

A leak detector (190) includes a sensor head (260), a light source (200) optically coupled to the sensor head and operable to generate excitation light. A detector (205) is optically coupled to the sensor head and operable to detect fluorescence light. A signal processing unit (210) is coupled to the detector and operable to signal a leak condition responsive to an intensity of the fluorescence light exceeding a threshold. A fluid-tight enclosure (235) encloses at least the light source, the detector, and the signal processing unit.

24 Claims, 7 Drawing Sheets

OPTICAL LEAK DETECTOR FOR SUBSEA EQUIPMENT

BACKGROUND OF THE INVENTION

The disclosed subject matter relates generally to subsea hydrocarbon production and, more particularly, to an optical leak detector for detecting material leakage from subsea equipment.

To control a subsea well, a connection is established between the well and a monitoring and control station. The monitoring and control station may be located on a platform or floating vessel near the subsea installation, or alternatively in a more remote land station. The connection between the control station and the subsea installation is usually established by installing an umbilical between the two points. The umbilical may include hydraulic lines for supplying hydraulic fluid to various hydraulic actuators located on or near the well. The umbilical may also include electrical and or fiber optic lines for supplying electric power and also for communicating control signals and/or well data between the control station and the various monitoring and control devices located on or near the well.

Hydrocarbon production from the subsea well is controlled by a number of valves that are assembled into a unitary structure generally referred to as a Christmas tree. Christmas tree and wellhead systems have the principle functions of providing an interface to the in-well environment, allowing flow regulation and measurement, and permitting intervention on the well or downhole systems during the operational life of the well. The actuation of the valves in the Christmas tree is normally provided using hydraulic fluid to power hydraulic actuators that operate the valves. Hydraulic fluid is normally supplied through an umbilical running from a remote station located on a vessel or platform at the surface. Alternative systems using electrically based actuators are also possible.

The subsea equipment includes many possible leakage paths, such as valves, pipe junction actuators, flanges, pipe connectors, jumpers, seals, etc. The detection of leaks of hydrocarbons, hydraulic fluids, tracers and other chemicals from underwater structures is an important requirement in enhancing the environmental and operational efficiency of underwater systems such as Christmas trees and subsea processing systems. A range of underwater leak detection systems have been developed including those based on acoustic, fluorescence, temperature and gas measurements. Often these are designed to be used as part of survey operations, but in a few instances as permanent monitors. Such devices are typically portable and are mounted to mobile devices, such as remotely operated vehicles (ROVs).

Acoustic devices are capable of detecting leaks from a wide area via the noise that may be produced by material leaking from underwater structures. Such acoustic systems detect only the secondary effect of the leak (i.e., the noise), hence, the application of acoustic detectors is significantly restricted in noisy environments. Further, acoustic detectors are not generally able to accurately locate a leak.

This section of this document is intended to introduce various aspects of art that may be related to various aspects of the disclosed subject matter described and/or claimed below. This section provides background information to facilitate a better understanding of the various aspects of the disclosed subject matter. It should be understood that the statements in this section of this document are to be read in this light, and not as admissions of prior art. The disclosed subject matter is directed to overcoming, or at least reducing the effects of, one or more of the problems set forth above.

BRIEF SUMMARY OF THE INVENTION

The following presents a simplified summary of the disclosed subject matter in order to provide a basic understanding of some aspects of the disclosed subject matter. This summary is not an exhaustive overview of the disclosed subject matter. It is not intended to identify key or critical elements of the disclosed subject matter or to delineate the scope of the disclosed subject matter. Its sole purpose is to present some concepts in a simplified form as a prelude to the more detailed description that is discussed later.

One aspect of the disclosed subject matter is seen in a leak detector. The leak detector includes a sensor head, a light source optically coupled to the sensor head and operable to generate excitation light. A detector is optically coupled to the sensor head and operable to detect fluorescence light. A signal processing unit is coupled to the detector and operable to signal a leak condition responsive to an intensity of the fluorescence light exceeding a threshold. A fluid-tight enclosure encloses at least the light source, the detector, and the signal processing unit.

Another aspect of the disclosed subject matter is seen in a subsea leak detection system. The subsea leak detection system includes a subsea structure operable to contain a hydrocarbon material. A leak detection module includes a sensor head mounted proximate a source of potential leakage on the subsea structure, a light source optically coupled to the sensor head and operable to generate excitation light, a detector optically coupled to the sensor head and operable to detect fluorescence light, a signal processing unit coupled to the detector and operable to signal a leak condition responsive to an intensity of the fluorescence light exceeding a threshold, and a fluid-tight enclosure enclosing at least the light source, the detector, and the signal processing unit.

BRIEF DESCRIPTION OF THE SEVERAL VIEWS OF THE DRAWINGS

The disclosed subject matter will hereafter be described with reference to the accompanying drawings, wherein like reference numerals denote like elements, and.

While the disclosed subject matter is susceptible to various modifications and alternative forms, specific embodiments thereof have been shown by way of example in the drawings and are herein described in detail. It should be understood, however, that the description herein of specific embodiments is not intended to limit the disclosed subject matter to the particular forms disclosed, but on the contrary, the intention is to cover all modifications, equivalents, and alternatives falling within the spirit and scope of the disclosed subject matter as defined by the appended claims.

DETAILED DESCRIPTION OF THE INVENTION

One or more specific embodiments of the disclosed subject matter will be described below. It is specifically intended that the disclosed subject matter not be limited to the embodiments and illustrations contained herein, but include modified forms of those embodiments including portions of the embodiments and combinations of elements of different embodiments as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the disclosed subject matter unless explicitly indicated as being "critical" or "essential."

The disclosed subject matter will now be described with reference to the attached figures. Various structures, systems and devices are schematically depicted in the drawings for purposes of explanation only and so as to not obscure the disclosed subject matter with details that are well known to those skilled in the art. Nevertheless, the attached drawings are included to describe and explain illustrative examples of the disclosed subject matter. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Figure 1:
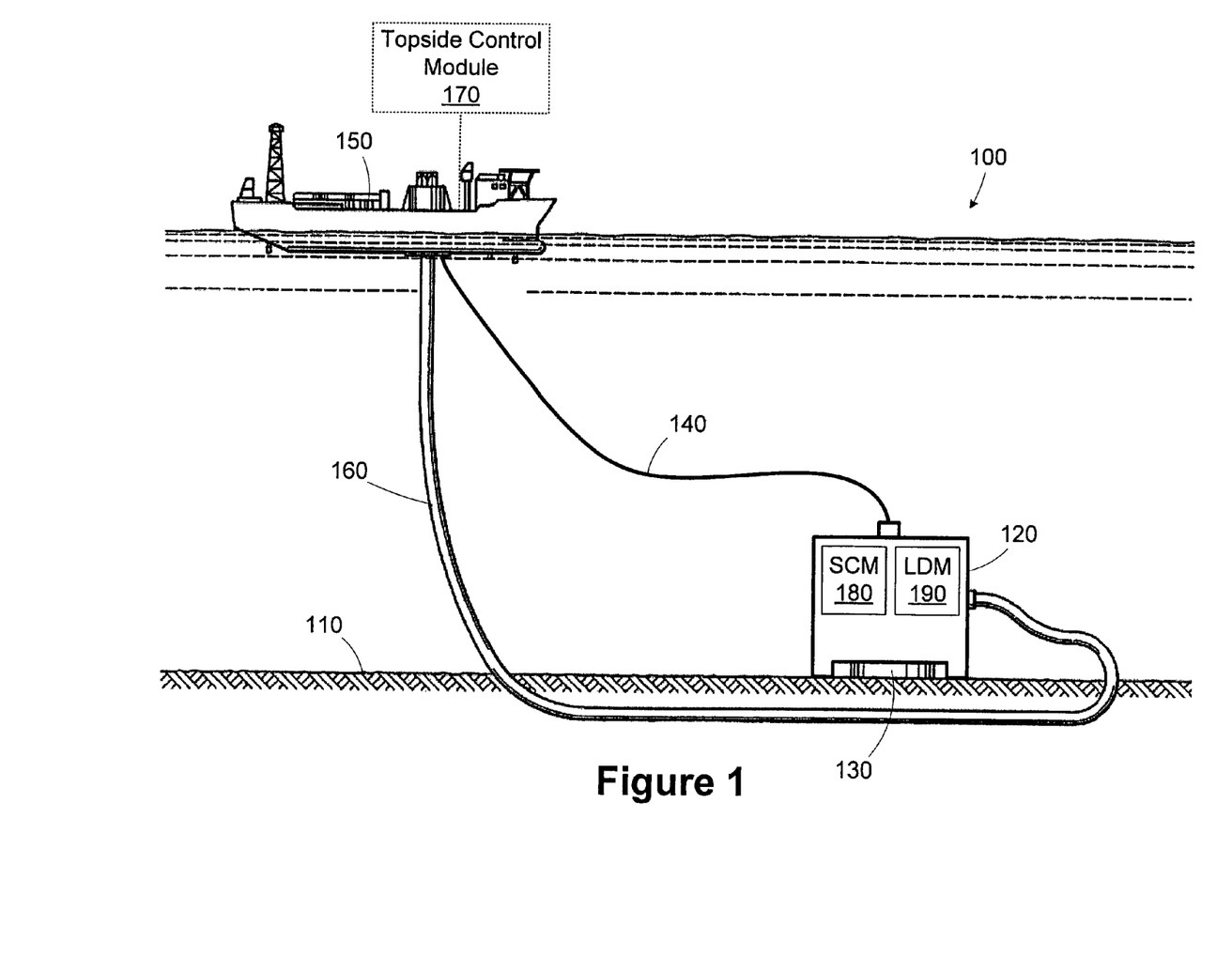
FIG. 1 is a simplified diagram of a subsea installation for hydrocarbon production.

Referring now to the drawings wherein like reference numbers correspond to similar components throughout the several views and, specifically, referring to FIG. 1, the disclosed subject matter shall be described in the context of a subsea installation 100 located on the seabed 110. The installation 100 includes a schematically depicted Christmas tree 120 mounted on a wellhead 130. The wellhead 130 is the uppermost part of a well (not shown) that extends down into the sea floor to a subterranean hydrocarbon formation. An umbilical cable 140 for communicating electrical signals, fiber optic signals, and/or hydraulic fluid extends from a vessel 150 to the Christmas tree 120. In other embodiments, the vessel 150 may be replaced by a floating platform or other such surface structure. In one illustrative embodiment, a flowline 160 also extends between the vessel 150 and the Christmas tree 120 for receiving hydrocarbon production from the well. In some cases, the flowline 160 and a communications line (not shown) may extend to a subsea manifold or to a land based processing facility. A topside control module (TCM) 170 is housed on the vessel 150 to allow oversight and control of the Christmas tree 120 by an operator.

A subsea control module (SCM) 180 is mounted to the Christmas tree 120 for receiving control signals from operators on the vessel 150 and for communicating data from various wellhead and downhole sensors to the TCM 170. A leak detection module (LDM) 190 provides local leak detection for various subsea components such as valves, pipe junction actuators, flanges, pipe connectors, jumpers, seals, etc. associated with the Christmas tree 120, umbilical 140, or flowline 160. In the illustrated embodiment, the LDM 190 interfaces with the SCM 180 for communicating leak detection signals to the TCM 170. Alternatively, the LDM 190 may have its own communication interface, such as through the umbilical cord 140 for topside communication. The SCM 180 may automatically respond to leaks detected by the LDM 190 depending on the location and severity of the leak. Alternatively, the TCM 170 may control leak responses via automatic control or operator input.

Figure 2:
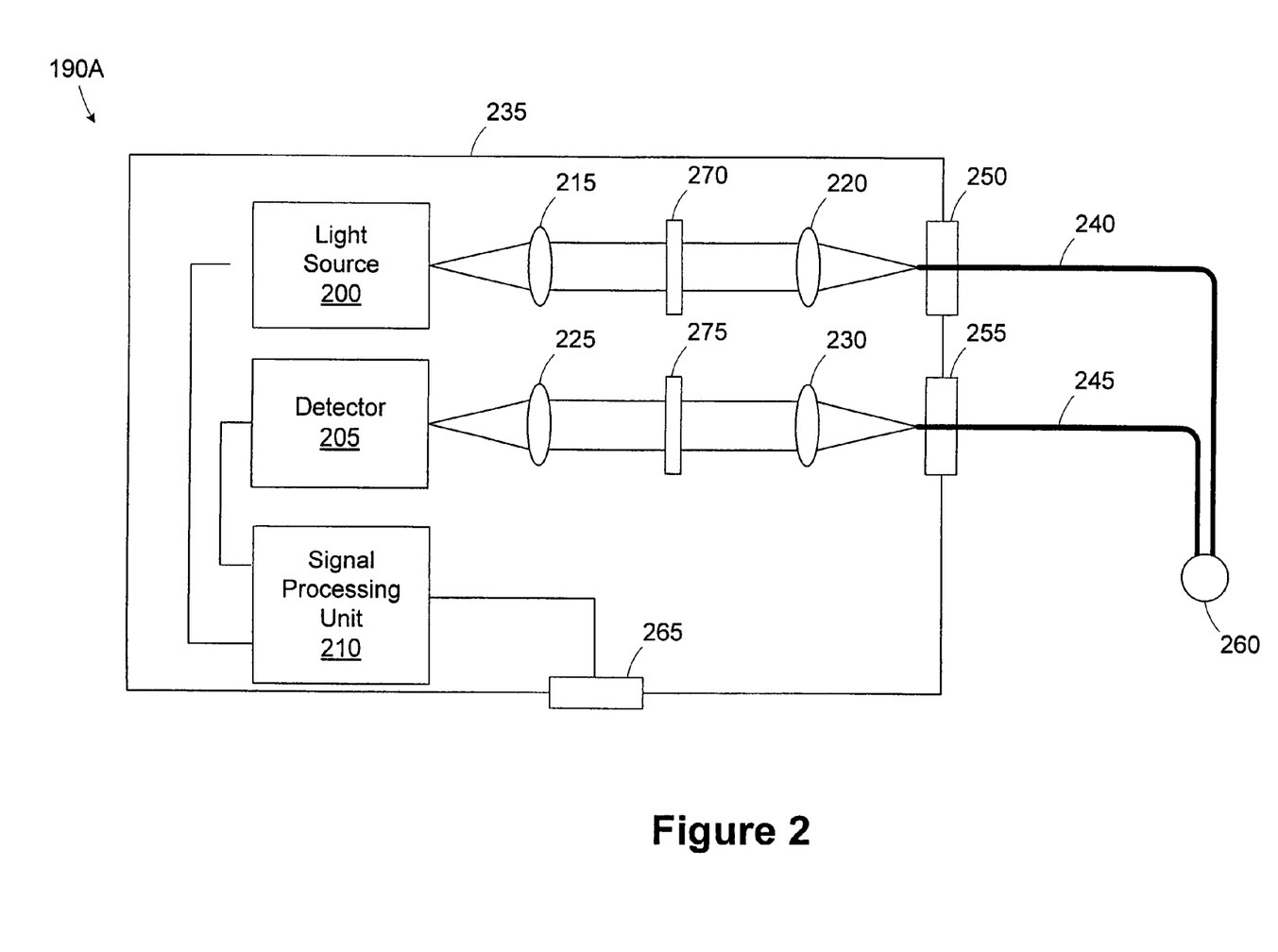
FIGS. 2-6 illustrate embodiments of a leak detection module in the system of FIG. 1.

FIG. 2 illustrates a simplified diagram of one embodiment of an LDM 190A. The LDM 190A includes a light source 200, detector 205, a signal processing unit 210, and optical lenses 215, 220, 225, 230 mounted in a water tight enclosure 235. Two optical fibers 240, 245 are coupled to the enclosure 235 via subsea optical connectors 250, 255. The excitation fiber 240 is coupled to the light source 200, and the detection fiber 245 is coupled to the detector 205. The optical fibers 240, 245 run to a sensor head 260 mounted near a source of potential leakage. An electrical connector 265 is provided for communicating between the LDM 190A and an external device, such as the SCM 180.

Although the LDM 190A is illustrated as having its own water tight enclosure 235, it is contemplated that the LDM 190A may be located in the same water tight enclosure as the SCM 180. The subsea optical connectors 250, 255 are optical feedthrough devices that allow the light to be transmitted across the pressure barrier while protecting the optoelectronics.

The excitation fiber 240 conveys excitation light from the light source 200, which emerges from the far end of the fiber 240 at the sensor head 260 in a cone. The characteristics of the cone depend on the numerical aperture of the excitation fiber 240 and the refractive index of the water. In some embodiments, an interference filter 270 is mounted between the light source 200 and the excitation fiber 240 (i.e., and between the lenses 215, 220 to remove wavelengths other than those useful for excitation. In yet other embodiments, the sensor head 260 may include a lens system fitted to the ends of the optical fibers 240, 245 to enhance the excitation and/or detection of the fluorescence or to vary the range from the sensor head were the fluorescence is collected.

The fluorescence light that is generated by the excitation light is collected by the detection fiber 245, which is located adjacent to the excitation fiber 240, but is held in the sensor head 260 at an angle with respect to the excitation fiber 240 (e.g., approximately 20 degrees). The light source 200 may be a broadband lamp, light emitting diode (LED), or laser that generates light of a wavelength suitable to excite the fluorescence of the leaking material. The excitation light is launched into the excitation fiber 240 using the lenses 215, 220. The collected fluorescence light emerging from the detection fiber 245 is passed to the detector 205.

In one embodiment, the detector 205 may be a spectrometer configured to detect light at the appropriate fluorescence wavelength (e.g., typically 350 nm-600 nm). The spectrometer may be implemented using a charge coupled device (CCD) to allow rapid collection and processing of the spectral information. Such a CCD may be operated in a DC mode or, alternatively, the CCD may be synchronized with a modulated or pulsed light source and employ time-gated detection. In either case, the output signal of the CCD at the fluorescence wavelength is related to the concentration of the leaking material in the water. The signal processing unit 210 receives the output of the detector 205 and identifies a potential leak and/or leak rate based on the magnitude of the florescence signal.

In another embodiment, an optical interference filter 275 may be used to filter the detection light to pass only the fluorescence wavelengths. In such an embodiment, the detector 205 may not analyze the entire spectrum, as with a spectrometer, but rather, the detector 205 may measure overall light intensity. A broadband detector, such as, but not limited to a photo diode or an avalanche diode may be used to implement the detector 205. The optical interference filter 275 would not be necessary in the embodiment where the detector 205 is a spectrometer.

Figure 3:
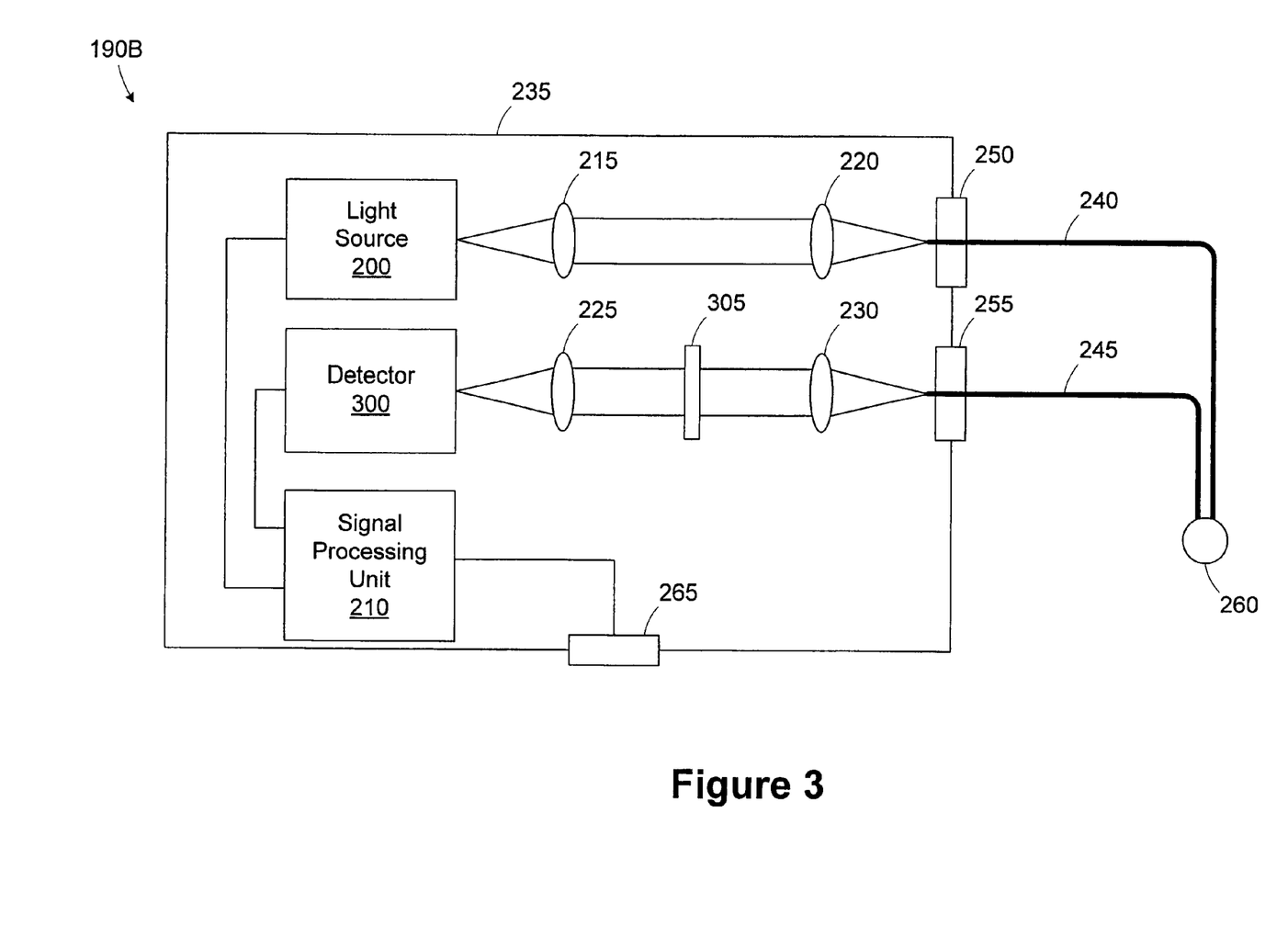

An alternative embodiment of an LDM 190B is shown in FIG. 3. The excitation light is amplitude modulated by the light source 200, and the detector 300 is a phase sensitive detector. In this embodiment, an optical interference filter 305 with a band pass corresponding to the peak fluorescence wavelength of the leaking material is fitted in front of the detector 300 between the lenses 225, 230 to reject background light. The collected fluorescence emerging from the detection optical fiber 245 is passed through this filter 305 and onto the detector 300. The resultant signal is processed using the phase sensitive detector 300 to provide an electrical output signal relating to the concentration of the leaking material. The signal processing unit 210 receives the output of the detector 300 and identifies a potential leak and/or leak rate based on the magnitude of the florescence signal.

Figure 4:
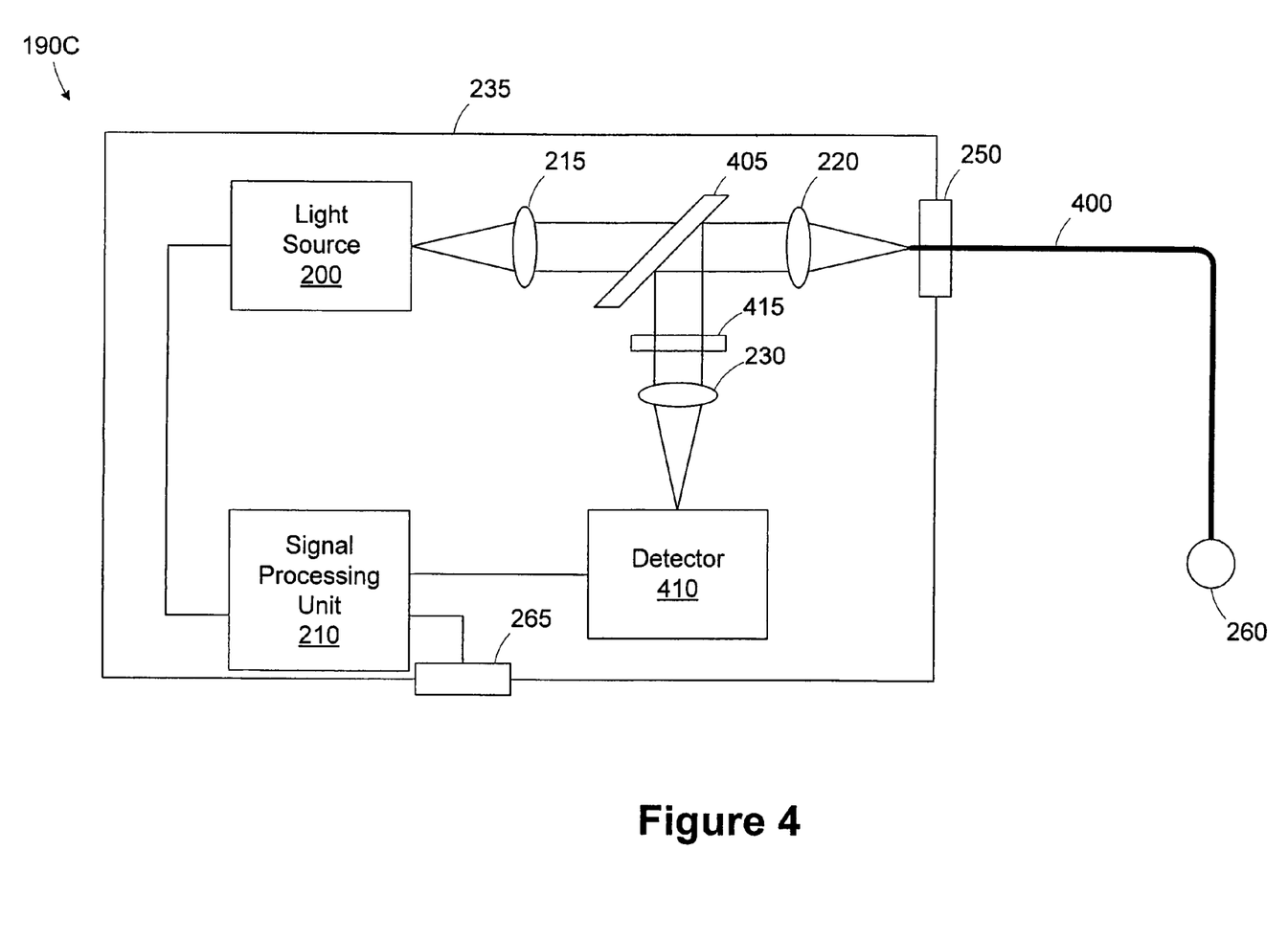

Another alternative embodiment of an LDM 190C is shown in FIG. 4. The LDM 190C, employs similar principles as the multi-fiber probes of FIG. 2 or 3, but employs only a single fiber 400 to deliver the excitation light and to capture the induced fluorescence of the leaking fluid. The excitation light passes through a beam splitter 405 before entering the fiber 400. The detection light resulting from the induced fluorescence is captured by the same fiber 400. Upon exiting the fiber 400, the fluorescent detection light is directed by the beam splitter 405 and passed to a detector 410. The detector 410 may be a phase sensitive detector, as described in reference to the embodiment of FIG. 3, or a spectrometer, photo diode, or avalanche diode as described in reference to the embodiment of FIG. 2. The optical interference filter 415 may be used in some embodiments.

In the various embodiments illustrated in FIGS. 2-4, a single monitoring location is illustrated. Multiple locations may also be monitored using a multi-optical fiber connector between the LDM 190 and the sensor heads 260. For example, an 8-fibre connector from HydroBond Engineering may be used. Using such a connector, multiple sensor systems within the LDM 190 may be used to access multiple locations.

Figure 5:
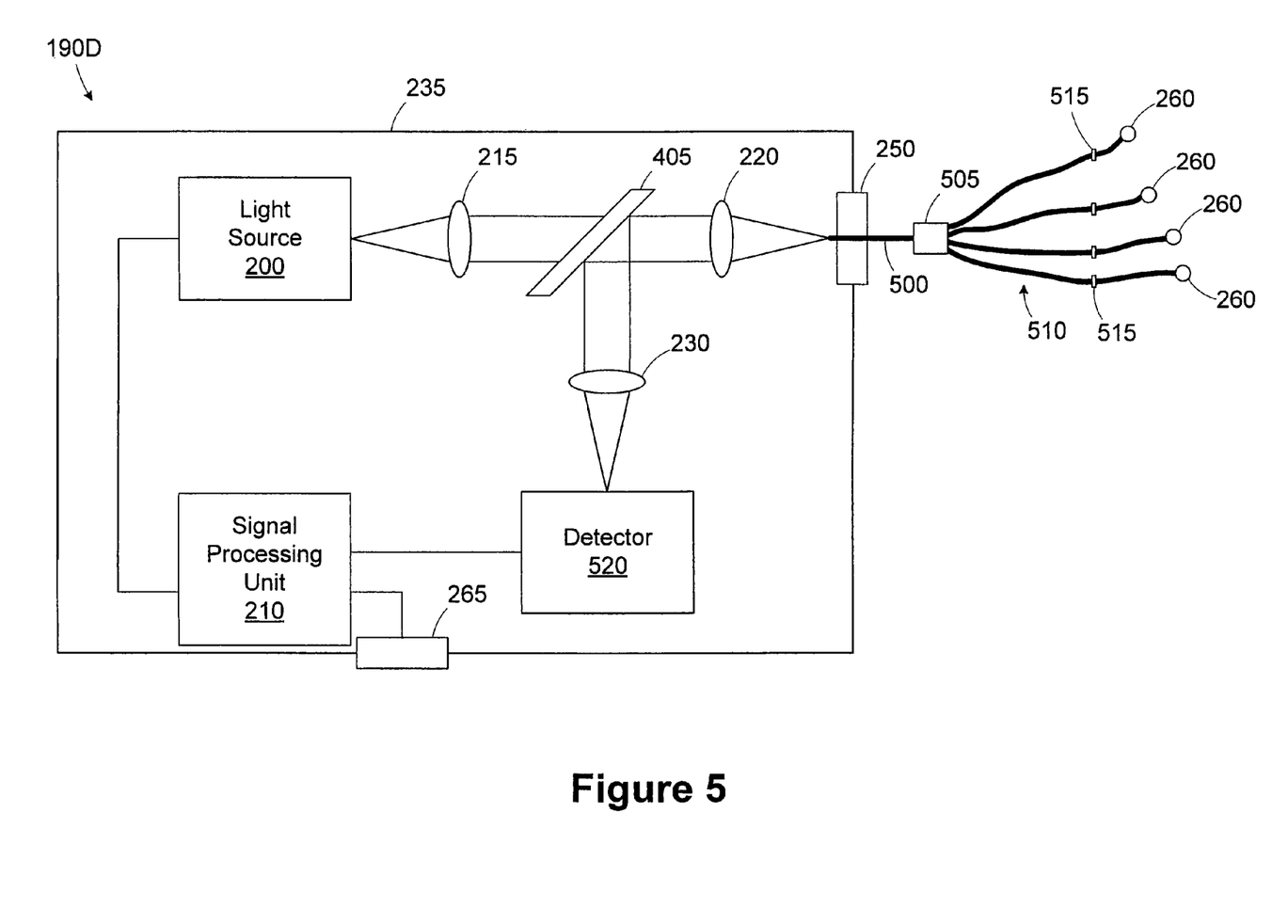

It is also contemplated that multiple locations may be monitored using shared hardware, depending on the particular application. For example, as illustrated in FIG. 5, the LDM 190D employs wavelength multiplexing. In this embodiment, a fiber 500 exiting the enclosure 235 runs to an optical coupler 505 that distributes individual fibers 510 to multiple locations. A wavelength selective component is incorporated into the optical fiber sensing heads 260. For example, an interference filter 515 may be attached to the fiber end or a Bragg grating (not shown) may be written into the fiber core. These wavelength selective components each have a distinct pass band which coincides with part of the fluorescence emission of the target species (i.e., oil or hydraulic fluid). The individual sensing heads 260 may be located at particular monitoring locations and each sensor head 260 distinguished at the detector 520 (e.g., spectrometer) by the specific wavelength range of the filter 515.

Figure 6:
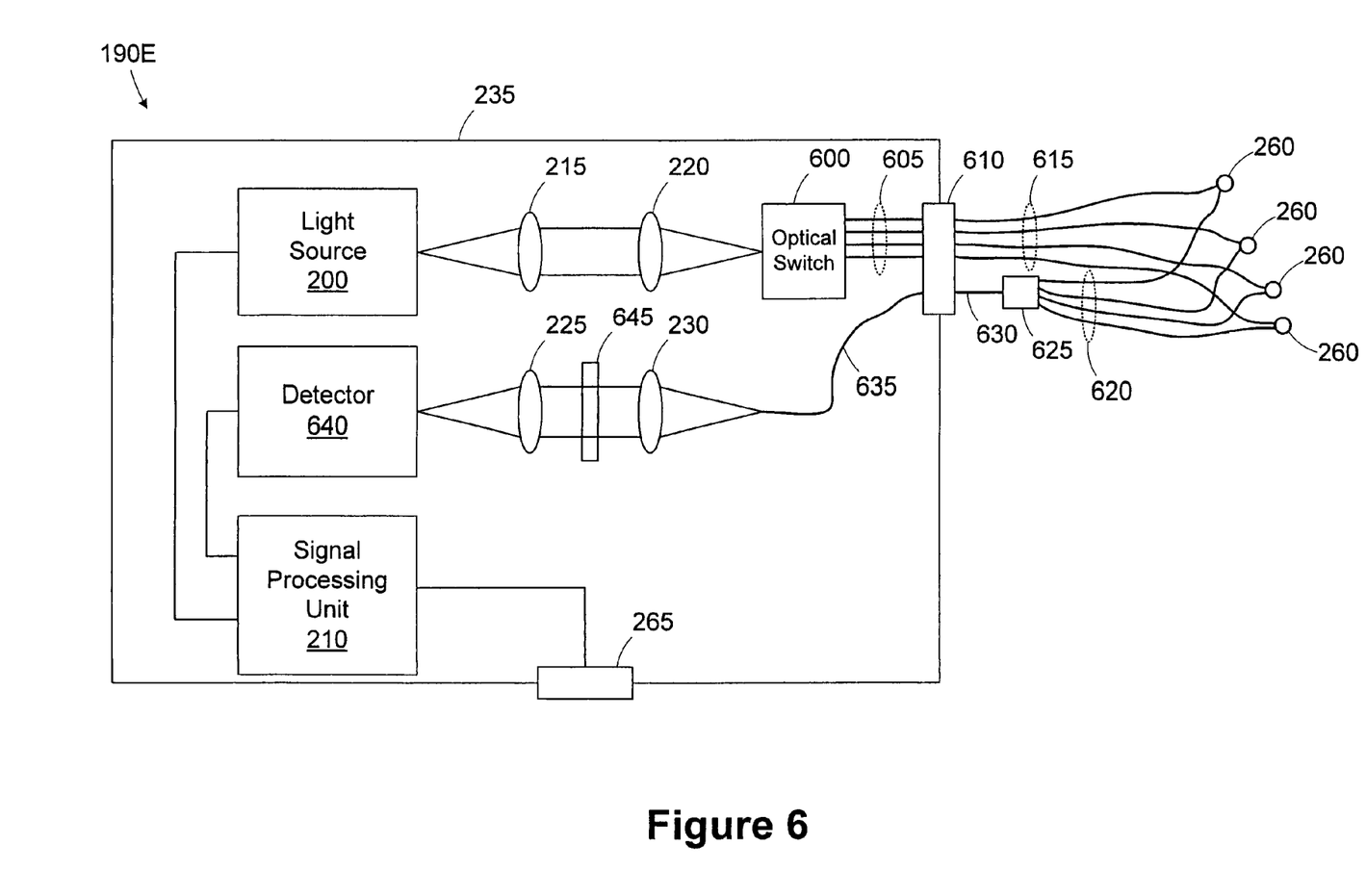

Alternatively, it is possible to use a variety of optical multiplexing arrangements to access multiple sensors from a single excitation and detection system. For example, as illustrated in the LDM 190E of FIG. 6, light from a single source 200 is transmitted to an optical switch 600, for example a 1×4 switch. The four output fibers 605 from the switch 600 are connected to separate fibers of a multi-fiber optical connector 610, and a plurality of connected fibers 615 on the subsea side of the connector 610 form the excitation fibers of a two-fiber sensor head 260 configuration. The sensor heads 260 may be placed at varying locations for leak monitoring. Detection fibers 620 for each of the 4 sensor heads 260 may be coupled to an optical fiber coupler 625 to reduce them into a single fiber 630, which is then fed to the connector 610. Alternatively, each detection fiber 620 may be connected to the connector 610, and subsequently multiplexed to the detector 640. On the inside of the water-tight enclosure 235, the detection fiber 635 is connected to the detector 640, which may be a spectrometer or other type of photo detector used with an interference filter 645. The individual sensor head 260 being monitored is determined by the setting of the optical switch 600, which only enables one sensor at a time. Monitoring of all four sensor heads 260 is performed by periodically enabling individual fibers 605. Of course, other types of multiplexing configurations may be used based on the teachings herein.

Figure 7:
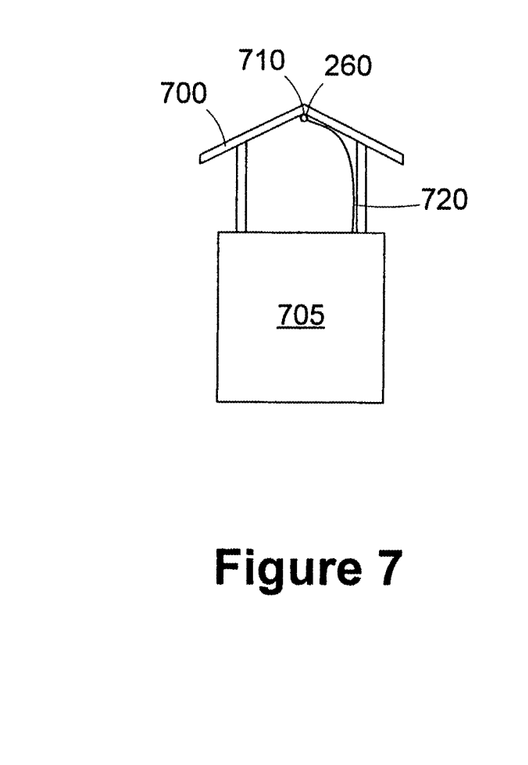
FIGS. 7-8 illustrate leak channeling devices that may be used with the leak detection module of FIG. 1.

In some embodiments the LDM 190 may be used in conjunction with a leak channeling device which directs the leaking material to the vicinity of the sensor head 260 or reduces the dispersion rate of the leaking fluid to allow detection. One exemplary channeling device includes a canopy 700, as illustrated in FIG. 7. The canopy 700 is positioned above a subsea structure 705 to collect lighter than water components (e.g., oil). In such arrangements the sensor head 260 is located proximate the highest point 710 of the underside of the canopy 700, and the optical cable 720 (i.e., containing one or more optical fibers) runs to the LDM 190 (not shown). The fluid collects under the canopy 700 to facilitate leak detection.

Figure 8:
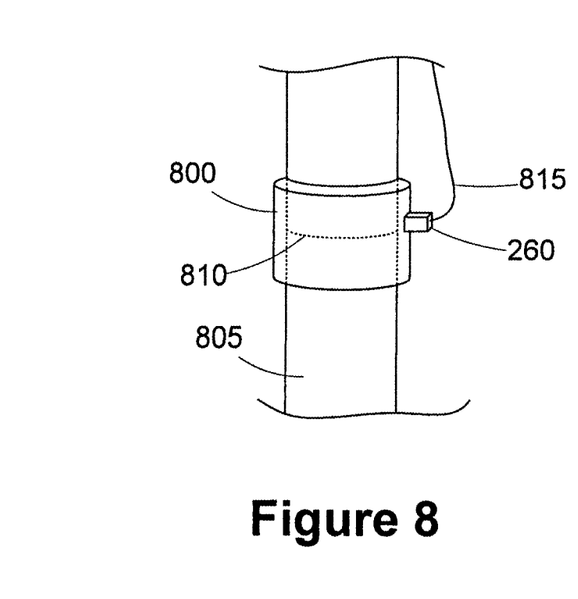

As illustrated in FIG. 8, another type of leak channeling device is a collar 800. The collar 800 may be mounted to cover a cylindrical structure 805, such as a pipe section near a flange or joint. The sensor head 260 monitors the annular region between the collar 800 and the structure 805. The collar 800 encloses the structure 805 at a potential leak location 810 to provide coverage for the entire outside diameter. Without such a collar 800, a leak on one side of the cylindrical structure 805 may not be detected if the sensor head 260 is positioned on the other side. In this arrangement, the collar 800 does not provide a pressure tight seal to the structure 805, but rather acts to slow dispersion of the leaking material so that is collects proximate the sensor head 260. The optical cable 815 runs to the LDM 190 (not shown).

In general for all of the embodiments illustrated, the signal processing unit 210 uses the fluorescence output signal to identify and quantify leakage at the monitored location. The signal processing unit 210 may signal a leak detection when the detection light intensity at the fluorescent wavelength passes a predetermined threshold. Increases in intensity past the detection threshold could be used to identify a leakage rate (i.e., quantitatively or qualitatively). To quantify a leak rate, qualification testing could be conducted to correlate the measured intensity to leak rate. The correlation between measured intensity and leak rate may depend on factors such as geometry, type of material, material dispersion rate, the presence of leak channeling devices, etc. The leak detection module 190 allows real-time leak detection and analysis.

The optical fiber fluorescence leak detection system embodiments described herein have numerous advantages. The leak detection module 190 may be installed permanently on a subsea structure. The leak detection module 190 may also be integrated with the existing well control instrumentation and communication schemes. A network of leak detection modules 190 may be employed to monitor many different paths of potential leakage on the subsea structure. The network may include individual leak detection modules 190 for each monitoring location or leak detection modules 190 that service multiple sensor heads.

The particular embodiments disclosed above are illustrative only, as the disclosed subject matter may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the disclosed subject matter. Accordingly, the protection sought herein is as set forth in the claims below.

We claim:

1. An underwater leak detector, comprising:
   a sensor head coupled to an end of at least one optical cable;
   a light source optically coupled to the sensor head via one the at least one optical cable, the light source being operable to generate excitation light that emerges from the sensor head in the shape of a cone;
   a detector optically coupled to receive detection light from the sensor head via the at least one optical cable, the detector being operable to detect fluorescence light in the detection light;
   a signal processing unit coupled to the detector and operable to signal a leak condition responsive to an intensity of the fluorescence light exceeding a threshold; and
   a fluid-tight enclosure enclosing at least the light source, the detector, and the signal processing unit, wherein the at least one optical cable is positioned between the fluid-tight enclosure and the sensor head.

2. The detector of claim 1, further comprising an interference filter mounted between the light source and the at least one optical cable.

3. The detector of claim 1, further comprising an interference filter mounted between the detector and the at least one optical cable.

4. The detector of claim 3, wherein the detector comprises at least one of a photo diode or an avalanche diode.

5. The detector of claim 1, further comprising an optical connector mounted on the fluid-tight enclosure for interfacing with the at least one optical cable through a pressure boundary defined by the fluid-tight enclosure.

6. The detector of claim 1, wherein the detector comprises a spectrometer.

7. The detector of claim 1, wherein the light source is operable to amplitude modulate the excitation light, and the detector comprises a phase sensitive photo detector.

8. The detector of claim 1, wherein the at least one optical cable comprises a single optical fiber that is coupled to the sensor head, the single optical fiber being operable to communicate the excitation light and the detection light, and the detector further comprises a beam splitter mounted between the light source and the single optical cable and operable to pass the excitation light to the single optical fiber and direct the detection light from the single optical fiber to the detector.

9. The detector of claim 1, further comprising a leak channeling device mounted to the sensor head.

10. The detector of claim 9, wherein the leak channeling device comprises a canopy having an underside surface, and the sensor head is mounted proximate a high point of the underside surface.

11. The detector of claim 9, wherein the leak channeling device comprises a collar.

12. The detector of claim 1, wherein the signal processing unit is operable to evaluate a leakage rate based on a magnitude of the intensity of the fluorescence light.

13. A subsea leak detection system, comprising:
    a subsea structure operable to contain a hydrocarbon material; and
    a leak detection module, comprising:
    a sensor head coupled to an end of at least one optical cable, the sensor head mounted proximate a source of potential leakage on the subsea structure;
    a light source optically coupled to the sensor head via the at least one optical cable, the light source being operable to generate excitation light that emerges from the sensor head in the shape of a cone;
    a detector optically coupled to receive detection light from the sensor head via the at least one optical cable, the detector being operable to detect fluorescence light in the detection light;
    a signal processing unit coupled to the detector and operable to signal a leak condition responsive to an intensity of the fluorescence light exceeding a threshold; and
    a fluid-tight enclosure enclosing at least the light source, the detector, and the signal processing unit, wherein the at least one optical cable is positioned between the fluid-tight enclosure and the sensor head.

14. The system of claim 13, further comprising:
    a topside control module;
    a subsea control module operable to control the subsea structure and to communicate with the topside control module, wherein the leak detection module is operable to communicate the leak detection to the control module.

15. The system of claim 13, further comprising a leak channeling device operable to collect leakage from the subsea structure, wherein the sensor head is mounted to the leak channeling device.

16. The system of claim 15, wherein the leak channeling device comprises a canopy having an underside surface, and the sensor head is mounted proximate a high point of the underside surface.

17. The system of claim 15, wherein the leak channeling device comprises a collar.

18. The system of claim 13, further comprising a plurality of additional sensor heads mounted proximate sources of potential leakage on the subsea structure, wherein each of the additional sensor heads is optically coupled to the light source and the detector.

19. The system of claim 18, wherein the leak detection module further comprises an optical coupler positioned between the additional sensor heads and the fluid-tight enclosure, wherein the optical encoder is adapted to employ wavelength multiplexing to communicate with at least the plurality of additional sensor heads.

20. The system of claim 18, wherein the leak detection module further comprises an optical switch that is adapted to employ optical switching to communicate with a selected one of the plurality of additonal sensor heads.

21. The system of claim 13, wherein the subsea structure comprises at least one of a Christmas tree, a well head, a valve, a joint, a flange, a pipe connector, a seal, or a jumper.

22. An underwater leak detector, comprising:
    a plurality of sensor heads, each of which is coupled to an end of one of a plurality of optical cables;
    a light source optically coupled to the each of the plurality of sensor heads via at least one of the plurality of optical cables, the light source being operable to generate excitation light that emerges from each of the plurality of sensor heads in the shape of a cone;

a detector optically coupled to receive detection light from each of the plurality of sensor heads, the detector being operable to detect fluorescence light in the detection light;

an optical coupler coupled to the light source and the detector, the optical encoder being adapted to distribute the excitation light to the plurality of sensor heads and direct the detection light from each of the plurality of sensor heads to the detector, wherein each of the plurality of optical cables is configured to filter the detection light using a bandpass range unique from the other plurality of optical cables;

a signal processing unit coupled to the detector and operable to signal a leak condition responsive to an intensity of the fluorescence light exceeding a threshold; and a fluid-tight enclosure enclosing at least the light source, the detector, and the signal processing unit, wherein the plurality of optical cables are positioned between the fluid-tight enclosure and the sensor head that is coupled to each of the plurality of optical cables.

23. An underwater leak detector, comprising:

a plurality of sensor heads, each of which is coupled to an end of one of a plurality of optical cables;

a light source optically coupled to the each of the plurality of sensor heads via at least one of the plurality of optical cables, the light source being operable to generate excitation light that emerges from each of the plurality of sensor heads in the shape of a cone;

a detector optically coupled to receive detection light from each of the plurality of sensor heads, the detector being operable to detect fluorescence light in the detection light;

an optical switch optically coupled to the light source and each of the plurality of sensor heads, the optical switch being operable to direct the excitation light to a selected one of the sensor heads;

a signal processing unit coupled to the detector and operable to signal a leak condition responsive to an intensity of the fluorescence light exceeding a threshold; and a fluid-tight enclosure enclosing at least the light source, the detector, and the signal processing unit, wherein the plurality of optical cables are positioned between the fluid-tight enclosure and the sensor head that is coupled to each of the plurality of optical cables.

24. The detector of claim 23, further comprising an optical coupler coupled to each of the sensor heads and operable to direct the detection light from the sensor heads to the detector.

* * * * *

UNITED STATES PATENT AND TRADEMARK OFFICE
CERTIFICATE OF CORRECTION

| | |
|---|---|
| PATENT NO. | : 8,927,924 B2 |
| APPLICATION NO. | : 13/254007 |
| DATED | : January 6, 2015 |
| INVENTOR(S) | : Daniel McStay et al. |

It is certified that error appears in the above-identified patent and that said Letters Patent is hereby corrected as shown below:

In the Claims,

Col. 7, line 22 (claim 1, line 3), delete the word "one" after the word "via".

Col. 8, line 58 (claim 20, line 4), change "additonal" to -- additional --.

Signed and Sealed this
Fourteenth Day of April, 2015

Michelle K. Lee
*Director of the United States Patent and Trademark Office*